US010215734B2

(12) United States Patent
Köber et al.

(10) Patent No.: US 10,215,734 B2
(45) Date of Patent: Feb. 26, 2019

(54) METHOD FOR TESTING A WORKPIECE USING ULTRASOUND

(71) Applicant: AREVA GmbH, Erlangen (DE)

(72) Inventors: Felix Köber, Erlangen (DE); Kerstin Scholz, Erlangen (DE); Edgar Zaus, Fürth (DE)

(73) Assignee: AREVA GMBH, Erlangen (DE)

( * ) Notice: Subject to any disclaimer, the term of this patent is extended or adjusted under 35 U.S.C. 154(b) by 192 days.

(21) Appl. No.: 15/120,436

(22) PCT Filed: Feb. 23, 2015

(86) PCT No.: PCT/EP2015/053699
§ 371 (c)(1),
(2) Date: Aug. 19, 2016

(87) PCT Pub. No.: WO2015/124762
PCT Pub. Date: Aug. 27, 2015

(65) Prior Publication Data
US 2017/0067855 A1 Mar. 9, 2017

(30) Foreign Application Priority Data
Feb. 24, 2014 (DE) .................. 10 2014 102 374

(51) Int. Cl.
G01N 29/26 (2006.01)
G01N 29/265 (2006.01)
G01N 29/11 (2006.01)

(52) U.S. Cl.
CPC .......... *G01N 29/11* (2013.01); *G01N 29/262* (2013.01); *G01N 29/265* (2013.01);
(Continued)

(58) Field of Classification Search
CPC .... G01N 29/11; G01N 29/262; G01N 29/265; G01N 2291/2636; G01N 2291/2638
(Continued)

(56) References Cited

U.S. PATENT DOCUMENTS

| 4,472,973 A | 9/1984 | Sugai et al. |
| 2005/0096542 A1 | 5/2005 | Weng et al. |

(Continued)

FOREIGN PATENT DOCUMENTS

| DE | 29 01 818 A1 | 7/1980 |
| DE | 196 17 455 A1 | 11/1997 |

(Continued)

OTHER PUBLICATIONS

International Application No. PCT/EP2015/053699 International Preliminary Report on Patentability Dated Sep. 9, 2016 (8 Pages).

*Primary Examiner* — J M Saint Surin
(74) *Attorney, Agent, or Firm* — Keller Jolley Preece

(57) ABSTRACT

The application relates to a method for testing a workpiece using ultrasound in a curved region of the surface of said workpiece, having the following steps: a plurality of ultrasonic signals are emitted from a plurality of transmitting positions into the workpiece a corresponding ultrasonic echo signal is received for each ultrasonic signal the ultrasonic echoes having amplitudes representing local maxima are determined for each transmitting position if an individual ultrasonic echo having an amplitude representing a local maximum was determined for a transmitting position in, the associated ultrasonic echo signal of said echo is selected if a plurality of ultrasonic echoes having an amplitude representing a local maximum were determined for a transmitting position, ultrasonic echo signals are selected if only an individual ultrasonic echo having an amplitude representing a local maximum was determined for an adjacent transmitting position at least the selected ultrasonic echo signals are evaluated.

7 Claims, 7 Drawing Sheets

(52) U.S. Cl.
CPC .............. *G01N 2291/2634* (2013.01); *G01N 2291/2636* (2013.01); *G01N 2291/2638* (2013.01)

(58) Field of Classification Search
USPC .......................................................... 73/628
See application file for complete search history.

(56) References Cited

U.S. PATENT DOCUMENTS

| | | | | |
|---|---|---|---|---|
| 2007/0056373 A1* | 3/2007 | Fischer | .................. | G01N 29/07 73/609 |
| 2007/0227249 A1* | 10/2007 | Meier | ................ | G01N 29/0645 73/628 |
| 2012/0060612 A1* | 3/2012 | Kleinert | ............... | G01N 29/043 73/632 |
| 2013/0160551 A1* | 6/2013 | Miura | .................. | G01N 29/341 73/598 |
| 2015/0330948 A1* | 11/2015 | Lingenberg | ............ | G01N 23/18 73/598 |

FOREIGN PATENT DOCUMENTS

| | | |
|---|---|---|
| DE | 10 2006 010 010 A1 | 9/2007 |
| DE | 10 2006 059 413 A1 | 6/2008 |
| EP | 1 830 185 A1 | 9/2007 |
| EP | 1 983 355 | 10/2008 |
| EP | 2 390 658 A1 | 11/2011 |
| EP | 2 653 862 A1 | 10/2013 |
| GB | 2 033 579 | 5/1980 |
| WO | WO 2008-010712 | 1/2008 |

\* cited by examiner

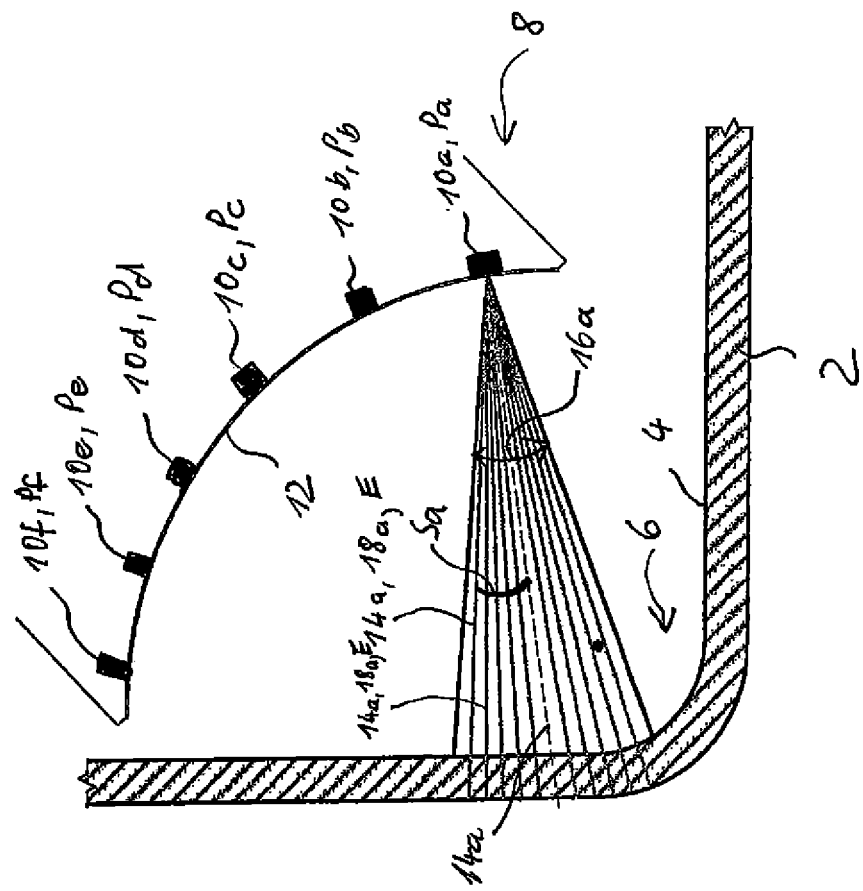

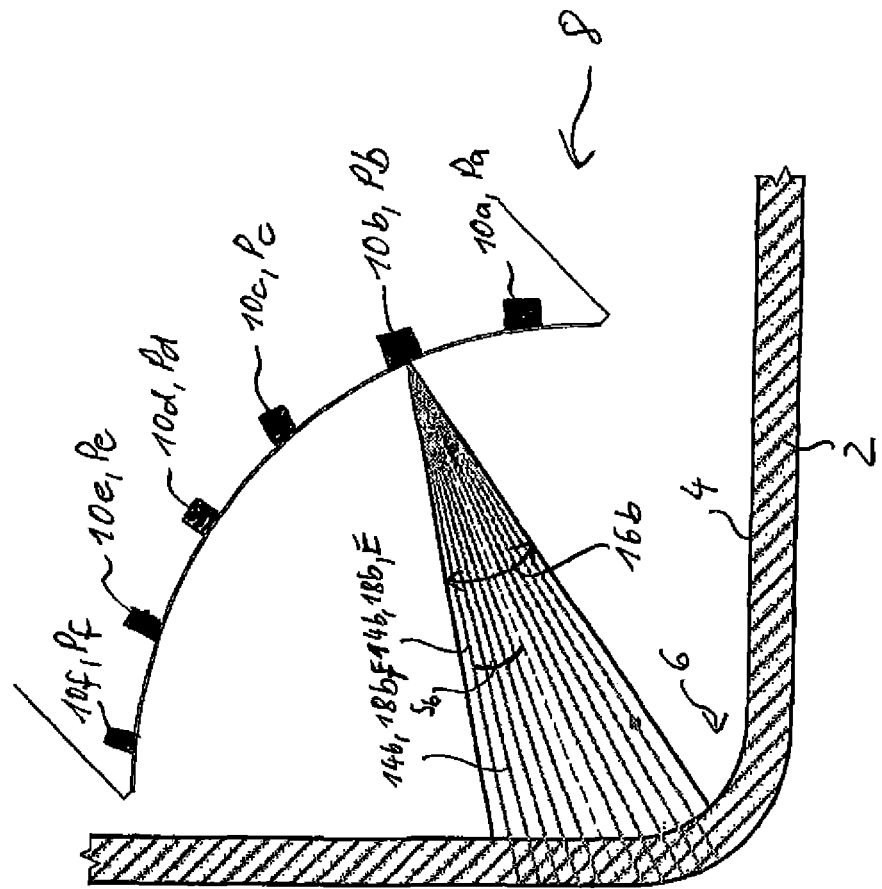

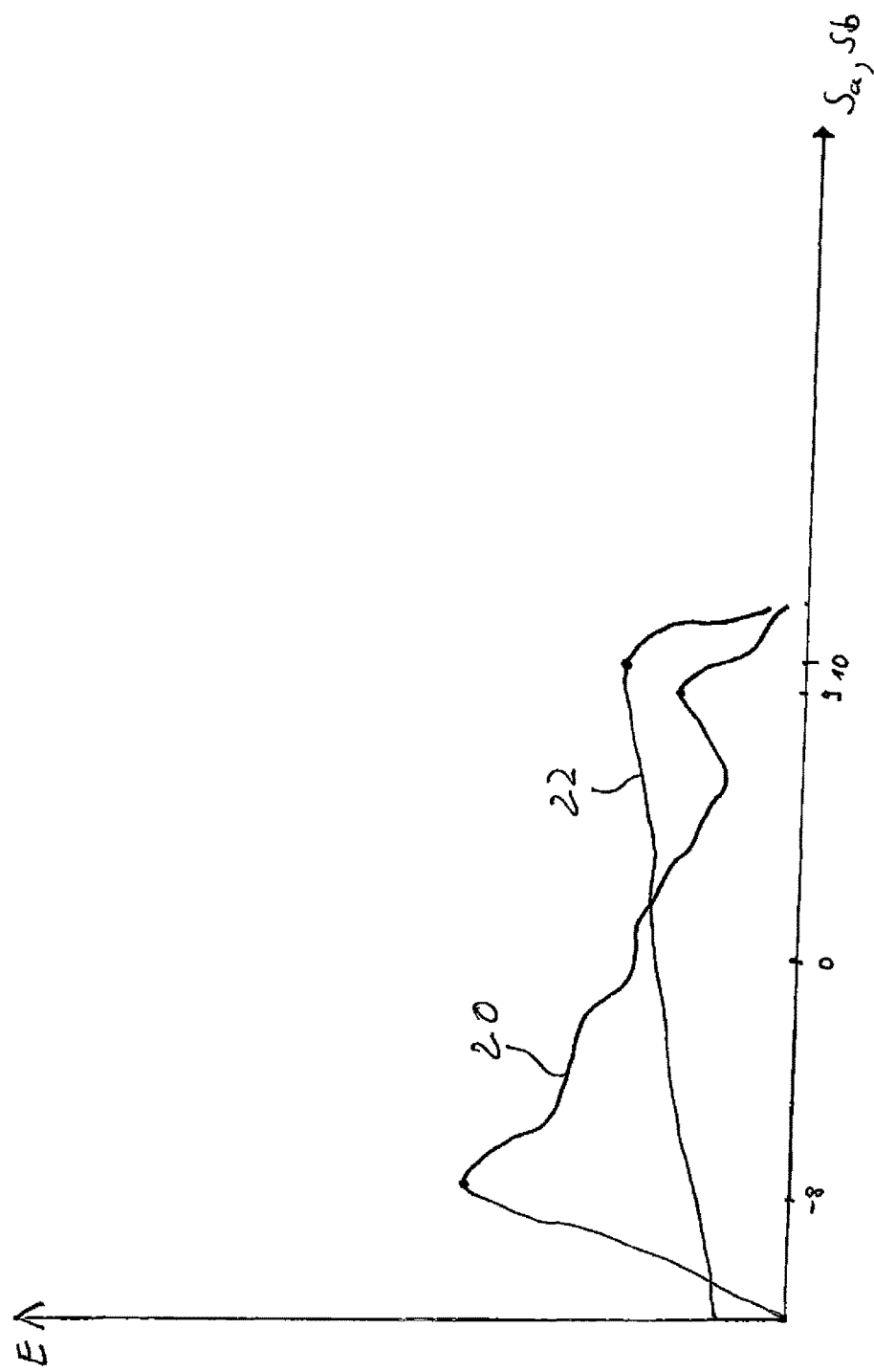

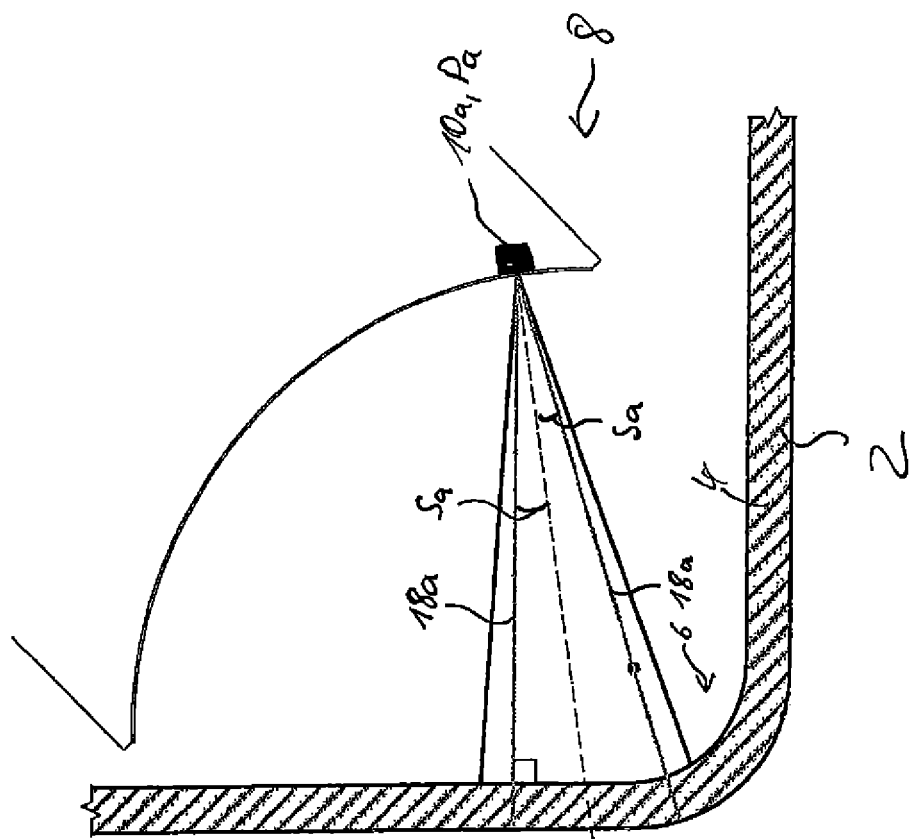

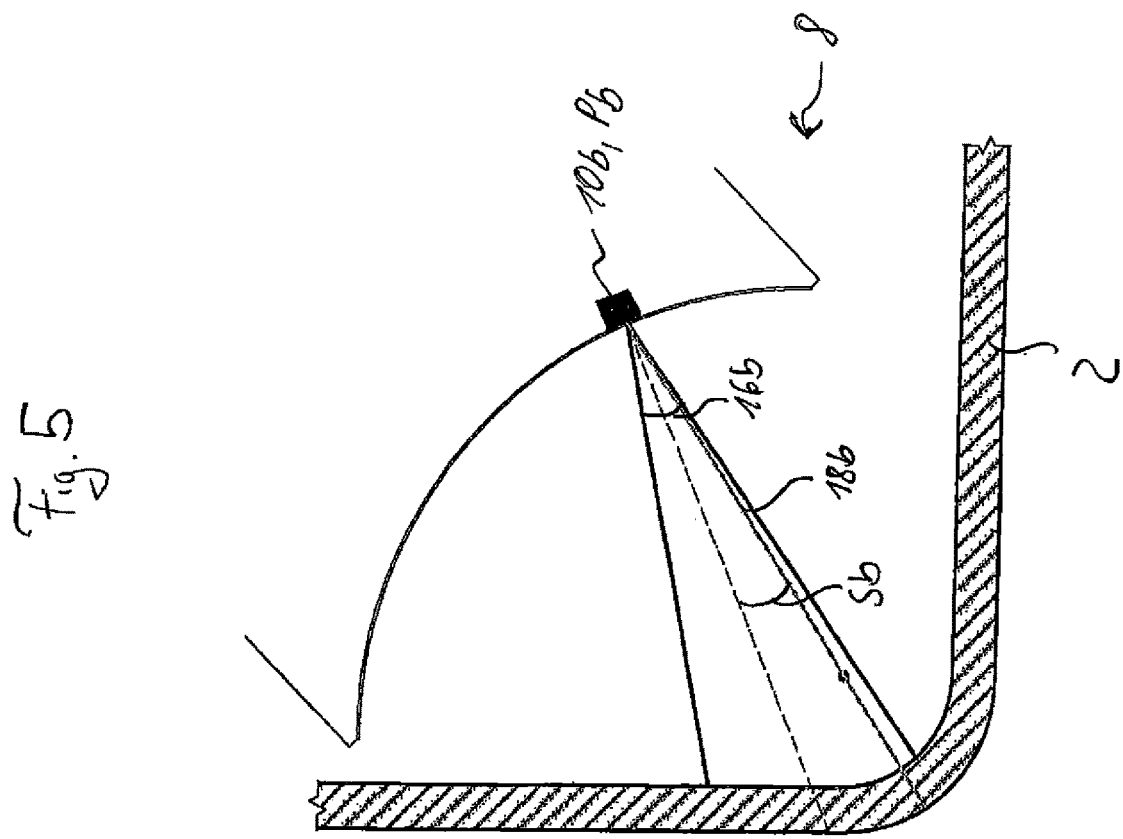

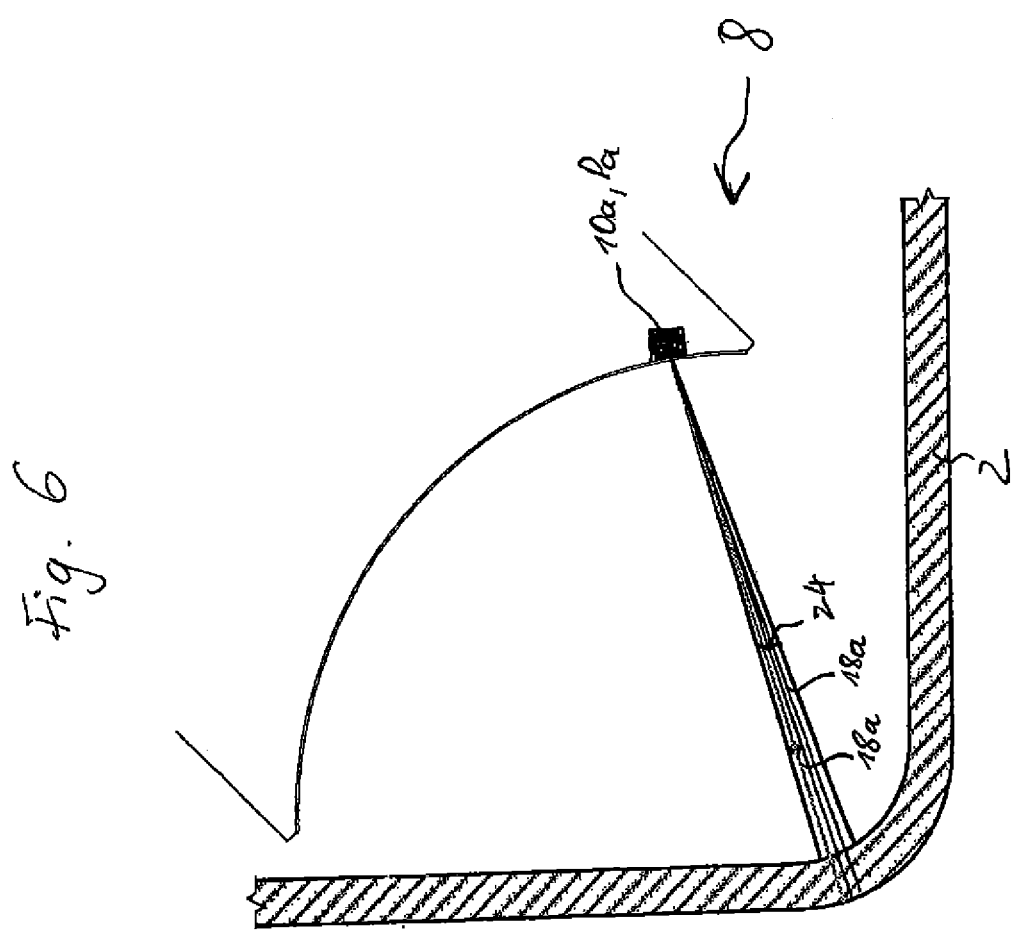

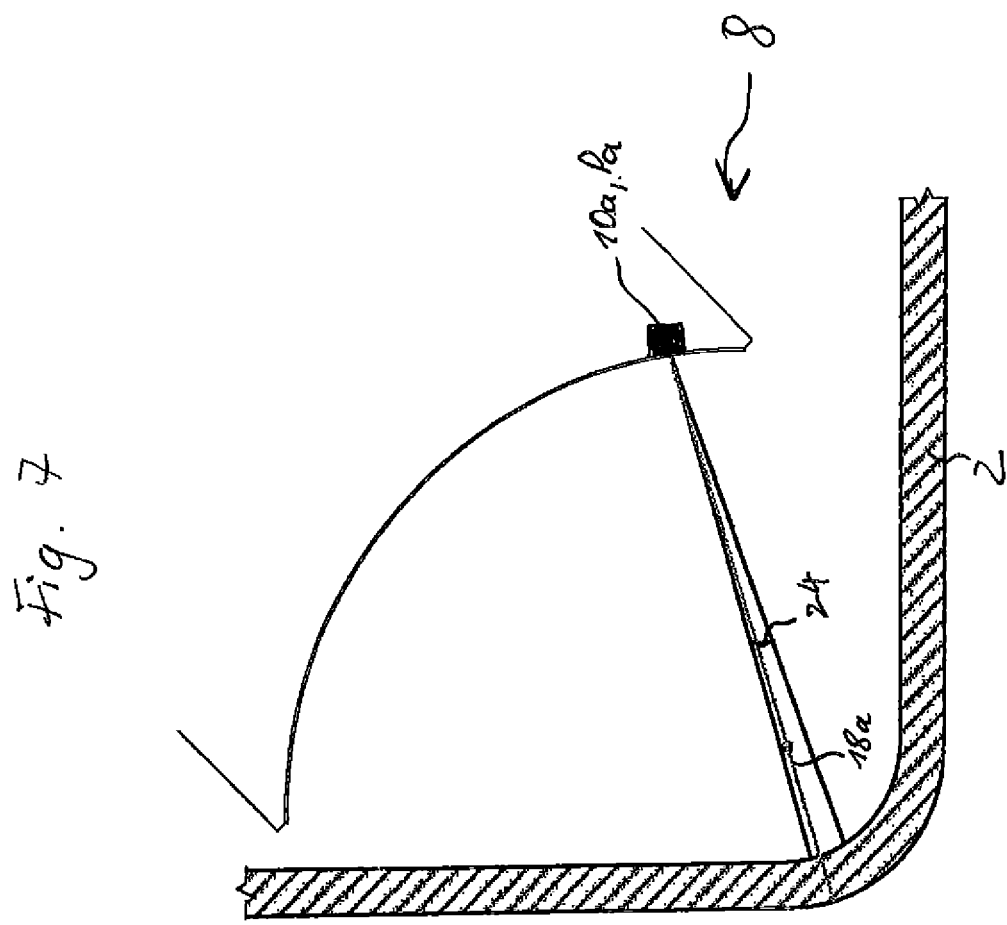

METHOD FOR TESTING A WORKPIECE USING ULTRASOUND

CROSS-REFERENCE TO RELATED APPLICATIONS

This application is a national phase entry under 35 U.S.C. § 371 of International Application No. PCT/EP2014/073544, filed Nov. 3, 2014, which claims the benefit of German Application No. 10 2013 112 136.5, filed Nov. 5, 2013. The entire contents of each of the foregoing Patent applications are hereby incorporated by reference.

BACKGROUND OF THE INVENTION

1. Field of the Invention.

The invention relates to a method for testing a workpiece by means of ultrasound in a curved area of its surface.

2. Background and Relevant Art.

In particular, workpieces produced from fiber composite materials such as glass-fiber reinforced or carbon-fiber reinforced plastics (GRP or CRP), can exhibit material faults due to the respective manufacturing method chosen, or following their deployment. In particular in the case of mechanically highly stressed and safety-relevant components, this is a major problem. Inspection of such materials is effected using non-destructive ultrasonic test techniques, in particular with a contact-free test, wherein an ultrasonic transducer generating an ultrasonic signal is not in direct contact with the workpiece. Rather, the ultrasound is coupled into the workpiece, for example via a fluid passageway. Contact-free test procedures have, among other things, the advantage that they have an optimum test coverage. But one disadvantage is that the ultrasonic transducer must be exactly positioned with respect to the workpiece in order to obtain a meaningful measurement or test result. But since the workpieces themselves, as well as the ultrasonic transducers or ultrasonic transducer arrangements that are used are subject to certain mechanical positioning inaccuracies, in particular for workpieces with areas with curved surfaces this can lead to measurements which do not provide a solid basis for drawing conclusions regarding the composition of the workpiece. A re-testing of the workpiece with corrected positions of the ultrasonic transducer relative to the workpiece must then be carried out.

SUMMARY OF THE INVENTION

It is the object of the present invention therefore to specify a method with which the above-mentioned disadvantages can be avoided.

This object is achieved according to the invention by means of a method having the features of claim 1. According to this, the method for testing a workpiece using ultrasound in a curved area of the surface of said workpiece comprises the following steps:

In step (a), a plurality of ultrasonic signals are emitted from a plurality of transmitting positions under different pivot angles lying in a pivoting range by means of at least one ultrasonic transducer and are coupled into the workpiece. The pivot angle is to be understood as meaning the angle enclosed between the vertical to the surface of the ultrasonic transducer and the direction of propagation of the ultrasonic signal.

In step (b) a corresponding ultrasonic echo signal is received for each ultrasonic signal and the amplitude of the ultrasonic echo generated upon entering the workpiece or on the rear wall of the workpiece is determined. Every ultrasonic echo signal thus comprises all ultrasonic echoes received, which are generated by the reflection of the corresponding emitted ultrasonic signal, for example upon its entry into the workpiece, on the rear wall of the workpiece or also due to material defects.

In step (c) for each transmitting position the ultrasonic echoes having amplitudes representing local maxima are determined and the ultrasonic echo signals of these are selected. The amplitudes of all ultrasonic echo signals measured in step (b), seen over the entire pivoting range, are therefore subjected to a quantitative evaluation. The ultrasonic echoes determined are those which represent a local maximum with respect to the other amplitudes. Therefore, it may be the case that for one or more transmitting positions, multiple local maxima exist. From the multiplicity of the ultrasonic echo signals, those signals will then be determined which have an ultrasonic echo with an amplitude representing a local maximum, wherein here also, a plurality of ultrasonic echo signals can therefore be selected in one or more transmitting positions. If, e.g. as a result of overdriving, a plurality of adjacent ultrasonic echo signals of a transmitting position have the same maximum amplitude value at the upper limit of the dynamic range, then the ultrasonic echo signal selected is always the one whose pivot angle has the smallest deviation from the integer mean value of the pivot angles of the relevant ultrasonic echo signals.

Then, in step (d1), if a single ultrasonic echo having an amplitude representing a local maximum has been determined for a transmitting position in step (c), the ultrasonic echo signal of said echo is selected.

If in step (c) a plurality of ultrasonic echoes having an amplitude representing a local maximum have been determined for a transmitting position, or if this is predefined for a transmitting position, in step (d2) a selection of ultrasonic echo signals is made, provided only a single ultrasonic echo having an amplitude representing a local maximum has been determined in step (c) for an adjacent transmitting position, by selecting those ultrasonic echo signals which lie in a specific angle range around the corresponding pivot angle of the ultrasonic echo signal having the maximum amplitude of the ultrasonic echo of the adjacent transmitting position and which have an ultrasonic echo having a maximum amplitude. The implementation of step (d2) therefore takes place if no unique result for an ultrasonic echo with maximum amplitude has been determined in step (c), or if this has been specified as such from the outset. The latter can take place, for example, when certain conditions are already known in advance, and the subsequent selection of ultrasonic echo signals can therefore be restricted to a known angle range. An additional selection is then made on the basis of geometric aspects in relation to selected ultrasonic echo signals of one or more adjacent transmitting positions. As part of this, the pivot angle of the selected ultrasonic echo signal is therefore transferred to the transmitting position under consideration and extended by a specific angle range. The ultrasonic echo signal having the maximum amplitude within the angle range is then selected. If, e.g. as a result of overdriving, a plurality of adjacent ultrasonic echo signals of a transmitting position within the angle range have the same maximum amplitude value at the upper limit of the dynamic range, then the ultrasonic echo signal selected is always the one whose pivot angle has the smallest deviation from the integer mean value of the pivot angles of the relevant ultrasonic echo signals.

In step (e) an evaluation of at least the selected ultrasonic echo signals is then carried out. The selected ultrasonic echo signals thus represent a basis for the remainder of the evaluation procedure and hence for the assessment of the material quality of the workpiece. The remaining ultrasonic echo signals can in the extreme case be discarded. Additional ultrasonic echo signals can also be included in the additional evaluation.

The invention is based on the recognition that the amplitude of the ultrasonic echo upon entering the workpiece is at maximum and is ideal for the evaluation when the injection axis pointing in the direction of propagation of the ultrasonic signal is oriented perpendicular to the tangent to the surface of the workpiece at the entry point of the sound. This is because in this condition, the reflected ultrasound, i.e. the ultrasonic echo generated upon entering the workpiece, is reflected with the smallest deflection relative to the ultrasonic source, i.e. the ultrasonic transducer.

By the detection of a plurality of ultrasonic echo signals that are based on the sound irradiation from a plurality of ultrasonic signals under different pivot angles lying in a pivoting range, a subsequent determination and evaluation of the amplitudes of the ultrasonic echoes which are produced upon entering the workpiece or by the rear wall of the workpiece, and by the selection according to the invention of the ideal ultrasonic echo signals, it is possible by evaluating at least these selected ultrasonic echo signals to obtain a valid test result almost independently of the positioning of the ultrasonic transducer.

From the plurality of the different ultrasonic echo signals only those are selected for which a local maximum ultrasonic echo signal is obtained upon entering the workpiece or from the rear wall of the workpiece. If in step (c) a plurality of ultrasonic echoes with an amplitude representing a local maximum are determined for a transmitting position, or if this is predefined for a transmitting position, then for this transmitting position a selection is made on the basis of an adjacency criterion. This is directed towards those echo signals selected in step (c), which have already been identified for an adjacent transmitting position. A specific angle range about the ultrasonic signal or ultrasonic echo signal is then defined, in which the most favorable ultrasonic echo signal must lie, and only this one is selected.

The advantage of this method is that different sound irradiations are carried out from permanently predefined transmitting positions under different pivot angles with only a single test operation. No re-positioning of the ultrasonic transducers is required, so that the test effort is reduced. The method allows large misalignment tolerances with regard to the workpiece and ultrasonic transducers, because the selection of the suitable ultrasonic echo signals means that during the evaluation at least those signals are considered in which an ideal ultrasonic echo signal is present.

In a preferred embodiment of the invention, a single ultrasonic transducer is moved into the plurality of transmitting positions. An arrangement of a plurality of ultrasonic transducers can also be used however, so that a change in the positioning of the individual ultrasonic transducer is not required during the testing of the workpiece.

By using a fixed geometric arrangement of the plurality of ultrasonic transducers, the individual transmitting positions are also defined at the same time due to the positioning of the whole arrangement relative to the workpiece.

Such an arrangement can comprise at least one phased array ultrasonic transducer. A change in the pivot angle for a transmitting position can be effected by electronic means. The ultrasonic transducer does not then need to be physically pivoted about a pivot axis. This allows the ultrasonic transducer to be designed even more compactly, because no space is then required for mechanical adjustment mechanisms. The testability or test coverage of workpieces which are difficult to access is thus improved. The duration of the test can also be reduced, since a physical pivoting, e.g. in a liquid, takes more time than an electronic pivoting.

For testing inner radii of the workpiece it is preferable to use an arrangement whose surface facing the workpiece has a concave curvature. This allows the arrangement to be made more compact compared with an arrangement with a flat surface.

In step (a) the ultrasonic signals are preferably each emitted one after the other.

In a further preferred embodiment of the invention the ultrasonic testing of the workpiece is effected in a contactless manner. For example, the test is carried out by means of immersion techniques, which means that the workpiece and the ultrasonic transducer or transducers are immersed in a liquid, and the ultrasound from the ultrasonic transducer is injected into the workpiece along this liquid path. In this case, with regard to the sound irradiation of the ultrasonic signal, no mechanical connection exists between the ultrasonic transducer and the workpiece to be tested. This technique can also be used to test difficult to reach areas of a workpiece. Furthermore, accurate matching of the ultrasonic transducer to the geometry of the surface is not required.

BRIEF DESCRIPTION OF THE DRAWINGS

To provide further explanation of the invention reference is made to the exemplary embodiments shown in the drawings. Shown are:

FIG. 1 an arrangement of a plurality of ultrasonic transducers and a workpiece during testing with a first ultrasonic transducer in a first transmitting position, FIG. 2 the arrangement of a plurality of ultrasonic transducers and the workpiece of FIG. 1 during testing with a further ultrasonic transducer in a further transmitting position, FIG. 3 a diagram showing the amplitude of the echo generated upon entering the workpiece as a function of the pivot angle, FIG. 4 the arrangement of a plurality of ultrasonic transducers and the workpiece with selected ultrasonic echo signals of the first transmitting position, FIG. 5 the arrangement of a plurality of ultrasonic transducers and the workpiece with selected ultrasonic echo signals of the further transmitting position, FIG. 6 the arrangement of a plurality of ultrasonic transducers and the workpiece with ultrasonic echo signals of the first transmitting position, said signals lying in an angle range, FIG. 7 the arrangement of a plurality of ultrasonic transducers and the workpiece with a selected ultrasonic echo signal of the first transmitting position.

DETAILED DESCRIPTION

FIG. 1 shows a workpiece 2 to be tested, whose surface comprises a curved area 6, here with a concave curvature about an angle of about 90°. The method is also suitable for differently curved surfaces 4 and in particular for concavely curved surfaces 4 with other angles. The surface 4 can also have different curvatures, such as convex and concave curvatures.

The workpiece 2 is tested using an ultrasonic immersion technique, which requires the workpiece 2 to be submerged in a liquid bath that is not shown. Furthermore, FIG. 1 shows an arrangement 8 of a plurality of, in this case six, ultrasonic transducers 10*a*, *b*, *c*, *d*, *e*, *f*, which are integrated in a test head. These are also immersed in the liquid bath. The ultrasonic transducers 10*a-f* are each operated in phased-array technology. The surface 12 of the ultrasonic test head, or of the arrangement 8, facing the workpiece 2 has a concave curvature.

The fixed geometrical arrangement of the ultrasonic transducers 10*a-f* within the arrangement 8 and a corresponding positioning of the arrangement 8 or of the ultrasonic test head with respect to the workpiece 2 simultaneously defines a plurality of transmitting positions $P_a$-$P_f$. This means that ultrasonic transducer 10*a* is positioned in the transmitting position $P_a$, ultrasonic transducer 10*b* in the transmitting position $P_b$ and the other ultrasonic transducers 10*c-f* are positioned in the corresponding transmitting positions $P_c$-$P_f$.

In a first step (a), first of all by means of the ultrasonic transducer 10*a* a plurality of ultrasonic signals 14*a* are now emitted from a transmitting position $P_a$ under different pivot angles $S_a$ lying in a pivoting range 16*a* and injected into the workpiece 2. In this case the plurality of ultrasonic signals 14*a* pass through a liquid, preferably water. The pivoting range 16*a* in this case comprises a total range of 24° with pivot angles Sa from −12° to 12°. The ultrasonic signal 14*a* with the pivot angle of 0° is shown dashed.

The individual ultrasonic signals 14*a* in this example are emitted at intervals of 2°.

In step (b), for each ultrasonic signal 14*a* a corresponding ultrasonic echo signal 18*a* is received, in this case by the ultrasonic transducer 10*a*. It would also be possible, however, for the corresponding ultrasonic echo signal 18*a* to also be received by a different receiving element. The ultrasonic echo signal 18*a* comprises a plurality of ultrasonic echoes E, e.g. an ultrasonic echo E, which is caused upon the entry of the ultrasonic signal into the workpiece 2, further ultrasonic echoes E caused by material defects in the workpiece 2, or also an ultrasonic echo E which is caused by reflection of the ultrasonic signal 14*a* at the rear wall of the workpiece 2. The amplitude of the ultrasonic echo E, generated either upon entering the workpiece 2 or at the rear wall of the workpiece 2, is then determined.

In step (c), the ultrasonic echoes E having amplitudes representing local maxima are first determined for the transmitting position $P_a$ and the ultrasonic echo signals 18*a* of these are selected.

Then in accordance with step (a) a further emission of a plurality of ultrasonic signals 14*b* by the ultrasonic transducer 10*b* takes place, wherein these are in turn emitted under different pivot angles $S_b$ lying in a pivoting range 16*b* and injected into the workpiece 2. The pivoting range 16*b* can comprise an equal angle range to that of the pivoting range 16*a*, thus in this example 24°. But it can also be different from this. Also the individual pivot angles $S_b$ can correspond to the pivot angles $S_a$, but can also be different to them, i.e. the interval between the pivot angles $S_b$ can be larger or smaller than the interval between the individual pivot angles $S_a$. The steps (b) and (c) are then carried out as appropriate for the transmitting position $P_b$. This situation is explained in more detail in FIG. 2. All of the steps (a), (b) and (c) are then carried out for all other transmitting positions $S_c$-$S_f$. In these as well, the individual parameters such as pivot angle $S_c$-$S_f$ or pivoting range 16*c-f* can also be varied individually.

FIG. 3 now shows a diagram in which a curve 20 and a curve 22 are shown. Curve 20 represents the amplitudes of the ultrasonic echoes E, which have been created upon the entry of the ultrasonic signal 14*a* into the workpiece 2, of the ultrasonic echo signals 18*a*, as a function of the pivot angle $S_a$. Analogously, curve 22 represents the amplitudes of the ultrasonic echoes E of the ultrasonic echo signal 18*b*. Curve 20 has two local maxima for pivot angles $S_a$ of −8° and +9°. Curve 22, however, has only one local maximum at a pivot angle $S_b$ of +10°. Thus, in accordance with step (c) a plurality of ultrasonic echoes E are determined having amplitudes representing local maxima for the transmitting position $P_a$, namely those belonging to the corresponding ultrasonic signals 18*a* with the pivot angles $S_a$ of −8° and +9°. For the transmitting position $P_b$ only the ultrasonic echo E having an amplitude representing a local maximum is determined, which belongs to the ultrasonic echo signal 18*b* with the pivot angle $S_b$ of +10°. In each case these are the ultrasonic echo signals 18*a*, 18*b* whose corresponding ultrasonic signals 14*a*, 14*b* are incident orthogonally on the surface 4 of the workpiece.

Because only a single ultrasonic echo E having an amplitude representing a local maximum was determined for the transmitting position $P_b$, in accordance with step (d1) its associated ultrasonic echo signal 18*b*, i.e. the one with the pivot angle $S_b$ of +10°, is selected.

The ultrasonic echo signals 18*a*, 18*b*, determined and selected respectively, are shown in FIGS. 4 and 5 in relation to the arrangement 8 and the workpiece 2. It can be seen in FIG. 4 that an ultrasonic echo signal 18*a* belonging to the echo signals E determined in step (c) is injected into the curved area 6 of the surface 4 of the workpiece, while the other ultrasonic echo signal 18*a* is situated above this area. For the additional evaluation however, only the ultrasonic echo signal 18*a*, which is injected into the curved area, is relevant.

In order to be able to carry out a selection of the relevant ultrasonic echo signal 18*a*, in step (d2) the selected ultrasonic echo signal 18*b* of the adjacent transmitting position $P_b$ is then considered. As shown in FIG. 6 in more detail, from the entirety of the large number of ultrasonic echo signals 18*a*, that ultrasonic echo signal is now selected which lies in a specific angle range 24, here for example, +−2° about the corresponding pivot angle $S_b$ of the ultrasonic echo signal 18*b*, and having the maximum amplitude of the ultrasonic echo E of the adjacent transmitting position $P_a$. The pivot angle $S_b$ of the ultrasonic echo signal 18*b* having the maximum amplitude of the ultrasonic echo E was determined in step (c) as +10°. The angle range 24 was predefined as +−2°. The relevant angle range 24 therefore comprises the pivot angles $S_a$ of +10°+−2°, thus from +8° to +12°, as shown in FIG. 6. In this angle range 24, all ultrasonic echo signals 18*a* are now considered and that ultrasonic echo signal 18*a* whose ultrasonic echo E has the maximum amplitude is selected. In this case the ultrasonic echo signal 18*a* with the pivot angle $S_a$ of +9° is selected. The result of this selection process is shown in FIG. 7.

In this case, only the ultrasonic echo signal 18*b* having the maximum amplitude of the ultrasonic echo E of an adjacent transmitting position $S_b$ is considered. In individual cases however, a plurality of adjacent transmitting positions S can also be considered, provided in step (c) transmitting positions S having a plurality of selected ultrasonic echo signals 18*a-f* have been determined.

Subsequently, an evaluation is carried out of at least the selected ultrasonic echo signals 18*a-f*. The remaining ultrasonic echo signals on the other hand can be discarded.

Such an approach therefore enables the workpiece 2, almost independently of the positioning of the arrangement of the ultrasonic test head 8, to be initially irradiated with a large number of ultrasonic signals 14 under highly varied geometric conditions, and then the ultrasonic echo signals 18a-f that are suitable for evaluation to be selected.

LIST OF REFERENCE NUMERALS 2 workpiece
4 surface
6 curved area
8 ultrasonic test head
10a, b, c, d, e, f ultrasonic transducer
12 surface
14a, b ultrasonic signal
16a, b pivoting range
18a, b ultrasonic echo signal
20 curve
22 curve
24 angle range
E ultrasonic echo
$P_{a,b,c,d,e,f}$ transmitting position
$S_{a,b}$ pivot angle

The invention claimed is:

1. A method for testing a workpiece using ultrasound in a curved area of a surface of said workpiece, having the following steps:
   (a) emitting a plurality of ultrasonic signals from a plurality of transmitting positions under different pivot angles lying in a pivoting range using at least one ultrasonic transducer and injecting the ultrasonic signals into the workpiece,
   (b) receiving a corresponding ultrasonic echo signal for each ultrasonic signal and determining the amplitude of the ultrasonic echo generated upon entering the workpiece or on a rear wall of the workpiece,
   (c) determining, for each transmitting position, the ultrasonic echoes having amplitudes representing local maxima,
   (d1) if a single ultrasonic echo having an amplitude representing a local maximum has been determined for a transmitting position in step (c), selecting the associated ultrasonic echo signal of said echo,
   (d2) if in step (c) a plurality of ultrasonic echoes having an amplitude representing a local maximum have been determined for a transmitting position, or if this is predefined for a transmitting position, making a selection of ultrasonic echo signals, provided only a single ultrasonic echo having an amplitude representing a local maximum has been determined in step (c) for an adjacent transmitting position, by selecting those ultrasonic echo signals which lie in a specific angle range around the corresponding pivot angle of the ultrasonic echo signal having the maximum amplitude of the ultrasonic echo of the adjacent transmitting position and which have an ultrasonic echo having a maximum amplitude,
   (e) performing an evaluation of at least the selected ultrasonic echo signals.

2. The method as claimed in claim 1, wherein emitting the plurality of ultrasonic signals from the plurality of transmitting positions comprises moving a single ultrasonic transducer into the plurality of transmitting positions.

3. The method as claimed in claim 1, further comprising using an arrangement of a plurality of ultrasonic transducers.

4. The method as claimed in claim 3, further comprising forming the arrangement using at least one phased-array ultrasonic transducer.

5. The method as claimed in claim 3, in which a surface of the arrangement facing the workpiece has a concave curvature.

6. The method as claimed in claim 1, wherein emitting the plurality of ultrasonic signals from the plurality of transmitting positions comprises emitting the ultrasonic signals one after the other.

7. The method as claimed in claim 1, wherein the testing of the workpiece is contactless.

* * * * *